United States Patent [19]

Beylin et al.

[11] Patent Number: 5,380,925
[45] Date of Patent: Jan. 10, 1995

[54] CYCLIC AMINO ACIDS AND DERIVATIVES THEREOF

[75] Inventors: Vladimir Beylin; Huai G. Chen; Om P. Goel, all of Ann Arbor; Mark E. Marlatt, Grass Lake; John G. Topliss, Ann Arbor, all of Mich.

[73] Assignee: Warner-Lambert Company, Morris Plains, N.J.

[21] Appl. No.: 109,797

[22] Filed: Aug. 20, 1993

Related U.S. Application Data

[62] Division of Ser. No. 872,742, Apr. 22, 1992, Pat. No. 5,264,577.

[51] Int. Cl.⁶ .................. C07C 229/14; C07C 233/47; C07B 55/00; C07D 215/38
[52] U.S. Cl. .................................... 562/443; 562/401; 562/403; 562/405; 560/19; 560/27; 560/38; 549/59; 549/70; 549/483; 549/475; 548/217; 548/255; 548/240; 548/253; 546/135; 546/169; 546/268; 546/136; 564/168; 564/169; 564/189; 544/355
[58] Field of Search ............... 562/401, 403, 405, 443; 560/19, 27, 38; 564/168, 169, 189; 549/59, 70, 483, 475; 548/217, 255, 240, 253; 546/135, 169, 268; 544/355

[56] References Cited

U.S. PATENT DOCUMENTS 3,888,900  6/1975  Houlihan et al. ............... 562/405
3,950,425  4/1976  van der Burg ................... 562/405

OTHER PUBLICATIONS

Nestor Jr. et al, Synthesis and Biological Activity of Some Very Hydrophobic Superagonist . . . J. Med. Chem. 1982, 25, 795-801.
Zhurnal Organicheskoi Khimii 1:2069-2071 (1965) Ryaboi, V. I. & Ginzburg, O. F.

*Primary Examiner*—Glennon H. Hollrah
*Assistant Examiner*—Deborah Lambkin
*Attorney, Agent, or Firm*—Francis J. Tinney

[57] ABSTRACT

Novel cyclic amino acids which are useful in preparing biologically active peptides as well as a process for the preparation of D and L enantiomers of the cyclic amino acids are described where an N-protected derivative of the racemic cyclic amino acid is treated with (−)cinchonidine and the resulting salt resolved into the desired enantiomers, as well as derivatives thereof and valuable intermediates used in the process.

1 Claim, No Drawings

CYCLIC AMINO ACIDS AND DERIVATIVES THEREOF

This is a divisional application of U.S. Ser. No. 07/872,742 filed Apr. 22, 1992.

BACKGROUND OF THE INVENTION

The present invention relates to novel cyclic amino acids and a process for the preparation of D and L enantiomers of the novel cyclic amino acids and derivatives thereof which are used to prepare biologically active peptides useful as pharmaceutical agents.

The development of peptides as therapeutic agents has been hindered by the short duration of action and lack of oral activity of this class of compounds. Thus, unnatural amino acids have been used to replace natural amino acids in order to prepare analogs with enhanced potency and metabolic stability. In some cases these analogs were orally active.

Yabe, Y., et al, *Chemical Pharmaceutical Bulletin*, Volume 24, pages 3149–3157 (1976) disclosed a series of Luteinizing Hormone-Releasing Hormone analogs containing various hydrophobic unnatural amino acid replacements at the 3-position with potent biological activity. Nestor, Jr., J. J., et al, *Journal of Medicinal Chemistry*, Volume 25, pages 795–801 (1982) disclosed a series of Luteinizing Hormone-Releasing Hormone analogs containing various hydrophobic unnatural amino acid replacements at the 6-position with potent biological activity.

U.S. Pat. No. 4,766,109 disclosed a series of hydrophobic peptides having antihypertensive activity. In some cases the peptides contained racemic 3,3-diphenylalanine as the unnatural hydrophobic amino acid.

Hsieh, K-H, et al, *Journal of Medicinal Chemistry*, 32: 898–903 (1989) disclosed a series of angiotensin II analogs in which the phenylalanine at the 8-position was replaced with various unnatural amino acids including racemic 3,3-diphenylalanine. The authors used racemic 3,3-diphenylalanine since they were unable to resolve this amino acid using hog kidney acylase and carboxypeptidase. The octapeptide diastereomeric mixture containing racemic 3,3-diphenylalanine was subsequently separated by countercurrent distribution into the L- and D-diastereomeric peptides. The authors reported that the peptide diastereomer containing L-3,3-diphenylalanine in place of L-phenylalanine at the 8-position produced a twofold increase in activity.

Josien, H., et al, *Tetrahedron Letters* 32: 6447–6550 (1991) disclosed an asymmetric synthesis of L-(+)-3,3-diphenylalanine from a sultam derived glycine imine. However, this asymmetric synthesis requires long reaction times and proceeds in only 46% overall yield and 95% diastereomeric excess.

Copending U.S. patent application Ser. No. 07/828,399 disclosed a process for the preparation of D(−) and L(+)-3,3-diphenylalanine and D(−) and L(+)-substituted 3,3-diphenylalanines and derivatives thereof which are used to prepare biologically active peptides useful as pharmaceutical agents.

Ryaboi, V. I. and Ginzburg, O. F., *Zhurnal Organicheskoi Khimii* 1: 2069–2071 (1965) disclosed the synthesis of xanthnydryl glycine (DL-α-amino-9H-xanthene-9-acetic acid).

The object of the present invention is to prepare conformationally restrained hydrophobic cyclic amino acids. We have surprisingly and unexpectedly found that a series of bridged 3,3-diphenylalanines are useful in preparing various biologically active peptide analogs. Additionally, we have found that this series of bridged 3,3-diphenylalanines can be resolved into the D and L enantiomers using (−)cinchonidine.

SUMMARY OF THE INVENTION

Accordingly, a first aspect of the present invention is a compound of Formula I

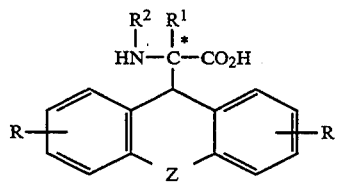

wherein Z is —O—,

—S(O)$_n$—, wherein n is zero or an integer of 1 or 2,

wherein R$^3$ is
  hydrogen,
  alkyl,
  alkenyl,
  alkynyl,
  cycloalkyl,
  cycloalkylalkyl,
  aryl,
  heteroaryl,
  fluorenylmethyl,
  CX$_3$, wherein X is halogen or aryl,
  —(CH$_2$)$_{\overline{m}}$, wherein m is an integer of 1, 2, 3, or 4, (CH$_2$)$_{\overline{n}}$CH=CH—(CH$_2$)$_{\overline{n}}$, wherein n is as defined above,

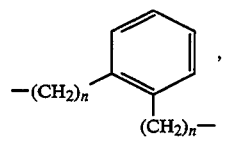

wherein n is as defined above,

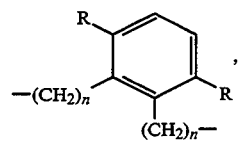

wherein R and n are as defined above,

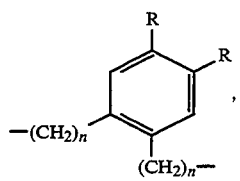

wherein R and n are as defined above,
(CH₂)ₙ̄C≡C—(CH₂)ₙ,
wherein n is as defined above,

wherein R³ is as defined above, and

wherein R³ is as defined above;
R is
hydrogen,
methyl,
trifluoromethyl,
methoxy,
hydroxy,
chloro,
bromo,
fluoro,
iodo,
2,4-dibromo,
2,4-dichloro, and
2,4-difluoro;
R¹ is
hydrogen,
alkyl,
alkenyl,
alkynyl,
cycloalkyl,
cycloalkylalkyl,
aryl,
arylalkyl,
heteroaryl, and
fluorenylmetnyl;
R² is
hydrogen,
benzyloxycarbonyl,
tertiary-butyloxycarbonyl,
fluorenyloxycarbonyl,
1-adamantyloxycarbonyl,
2-adamantyloxycarbonyl, and

wherein R³ is as defined above; stereochemistry at C is D, L, or DL; and with the exclusion of a compound of Formula I wherein
Z is —O—;

R is hydrogen;
R¹ is hydrogen;
R² is hydrogen; and stereochemistry at C is DL; or a pharmaceutically acceptable salt thereof.

A second aspect of the present invention is a process for the preparation of the D and L enantiomers of a compound of Formula I

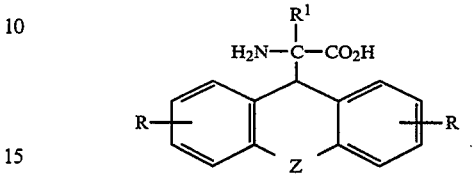

wherein Z is —O—,
—S(O)ₙ—,
wherein n is zero or an integer of 1 or 2,

wherein R³ is
hydrogen,
alkyl,
alkenyl,
alkynyl,
cycloalkyl,
cycloalkylalkyl,
aryl,
heteroaryl,
fluorenylmethyl,
CX₃,
wherein X is halogen or aryl,
—(CH₂)ₘ̄,
wherein m is an integer of 1, 2, 3, or 4,
(CH₂)ₙ̄CH=CH—(CH₂)ₙ̄,
wherein n is as defined above,

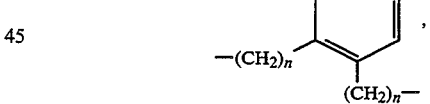

wherein n is as defined above,

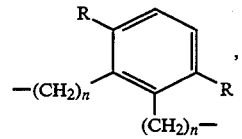

wherein R and n are as defined above,

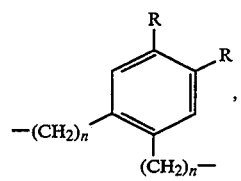

wherein R and n are as defined above, $(CH_2)_{\overline{n}}C\equiv C-(CH_2)_n$,
wherein n is as defined above,

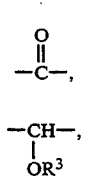

wherein $R^3$ is as defined above, and

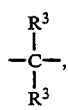

wherein $R^3$ is as defined above;
R is
  hydrogen,
  methyl,
  trifluoromethyl,
  methoxy,
  hydroxy,
  chloro,
  bromo,
  fluoro,
  iodo,
  2,4-dibromo,
  2,4-dichloro, and
  2,4-difluoro; and
$R^1$ is
  hydrogen,
  alkyl,
  alkenyl,
  alkynyl,
  cycloalkyl,
  cycloalkylalkyl,
  aryl,
  arylalkyl,
  heteroaryl, and
  fluorenylmethyl;
or a pharmaceutically acceptable salt thereof which comprises:

Step (a) treating a racemic compound of Formula II

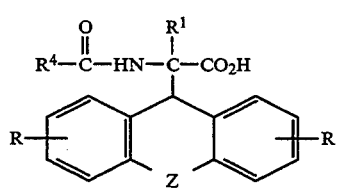

wherein $R^4$ is lower alkyl,
  $CX_3$ wherein X is hydrogen or halogen or aryl and R, $R^1$ and Z are as defined above, with (−)cinchonidine in a solvent to afford a racemic compound of Formula III;

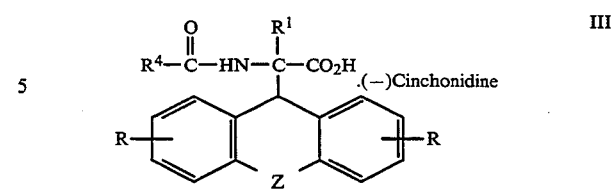

wherein R, $R^1$, $R^4$ and Z are as defined above;

Step (b) resolving a compound of Formula III R, $R^1$, $R^4$, and Z are as defined above by fractional crystallization into D and L enantiomers:

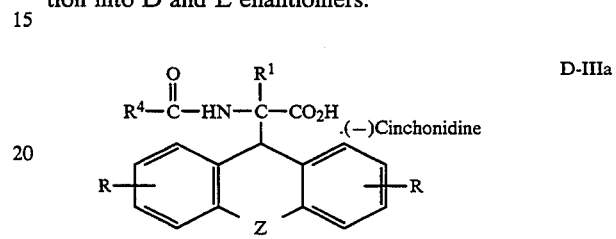

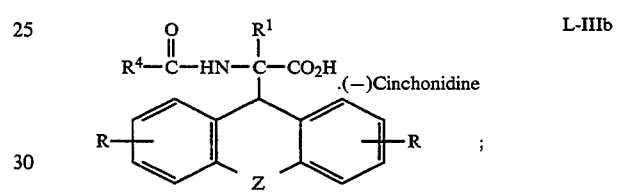

Step (c) treating a compound of Formula D-IIIa or Formula L-IIIb wherein R, $R^1$, $R^4$ and Z are as defined above with an acid in a solvent to afford a compound of Formula D-IIa or Formula L-IIb:

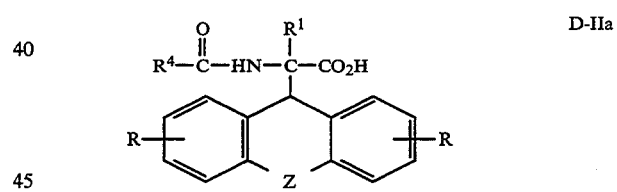

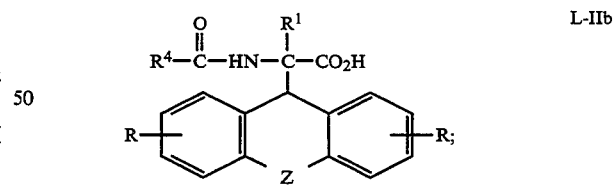

Step (d) heating a compound of Formula D-IIa or Formula L-IIb wherein R, $R^1$, $R^4$, and Z are as defined above with an acid to afford the D-Ia or L-Ib enantiomers of Formula I;

Step (e) and, if desired, converting a compound of Formula D-Ia or Formula L-Ib to a corresponding pharmaceutically acceptable salt by conventional means, and if so desired, converting the corresponding pharmaceutically acceptable salt to a compound of Formula D-Ia or Formula L-Ib by conventional means.

A third aspect of the present invention is a novel intermediate selected from the group consisting of

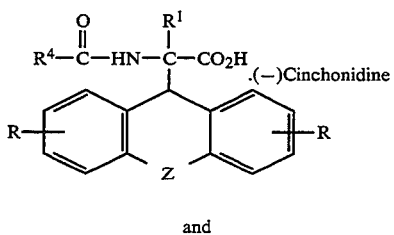

and

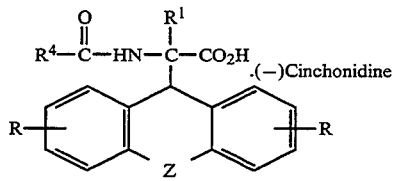

wherein Z is —O—, —S(O)$_n$—,
wherein n is zero or an integer of 1 or 2,

wherein R$^3$ is
  hydrogen,
  alkyl,
  alkenyl,
  alkynyl,
  cycloalkyl,
  cycloalkylalkyl,
  aryl,
  heteroaryl,
  fluorenylmethyl,
  CX$_3$,
wherein X is halogen or aryl,
  —(CH$_2$)$_{\overline{m}}$,
wherein m is an integer of 1, 2, 3, or 4,
  —(CH$_2$)$_{\overline{n}}$CH=CH—(CH$_2$)$_{\overline{n}}$,
wherein n is as defined above,

wherein n is as defined above, —(CH$_2$)$_{\overline{n}}$C≡C—(CH$_2$)$_n$,
wherein n is as defined above,

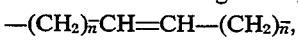

wherein R and n are as defined above,

D-IIIa

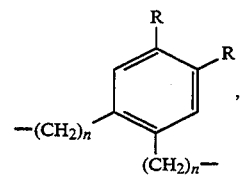

L-IIIb

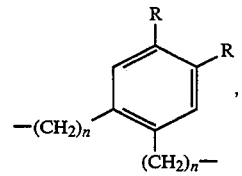

wherein R and n are as defined above,

wherein R$^3$ is as defined above, and

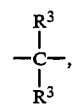

wherein R$^3$ is as defined above;
R is
  hydrogen,
  methyl,
  trifluoromethyl,
  methoxy,
  hydroxy,
  chloro,
  bromo,
  fluoro,
  iodo,
  2,4-dibromo,
  2,4-dichloro, and
  2,4-difluoro;
R$^1$ is
  hydrogen,
  alkyl,
  alkenyl,
  alkynyl,
  cycloalkyl,
  cycloalkylalkyl,
  aryl,
  arylalkyl,
  heteroaryl, and
  fluorenylmethyl;
and R$^4$ is
  lower alkyl,
  CX$_3$
wherein X is hydrogen or halogen or aryl.

DETAILED DESCRIPTION OF THE INVENTION

In the compounds of Formula I, the term "alkyl" means a straight or branched hydrocarbon radical having from 1 to 12 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, dodecyl, and the like.

The term "alkenyl" means a straight or branched unsaturated hydrocarbon radical having from 2 to 12 carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, and the like.

The term "alkynyl" means a straight or branched triple bonded unsaturated hydrocarbon radical having from 2 to 12 carbon atoms and includes, for example, ethynyl, 2-propynyl, 1-butynyl, 2-butynyl, 3-butynyl, 1-pentynyl, 3-pentyny 1,1-hexynyl, 2-hexynyl, 3-hexynyl, 3-heptynyl, 1-octynyl, 2-octynyl, 1-nonynyl, 2-nonynyl, 3-nonynyl, 4-nonynyl, 1-decynyl, 2-decynyl, 2-undecynyl, 3-undecynyl, 3-dodecynyl, and the like.

The term "cycloalkyl" means a saturated hydrocarbon ring which contains from 3 to 12 carbon atoms, for example, cyclopropyl, cyclobutyl, cyclopentyl, cyclohexyl, adamantyl, and the like.

The term "cycloalkylalkyl" means a saturated hydrocarbon ring attached to an alkyl group wherein alkyl is as defined above. The saturated hydrocarbon ring contains from 3 to 12 carbon atoms. Examples of such are cyclopropylmethyl, cyclopentylmethyl, cyclohexylmethyl, adamantylmethyl and the like.

The terms "alkoxy" and "thioalkoxy" are O-alkyl or S-alkyl as defined above for alkyl.

The term "aryl" means an aromatic radical which is a phenyl group, a benzyl group, a naphthyl group, a biphenyl group, a pyrenyl group, an anthracenyl group, or a fluorenyl group and the like, unsubstituted or substituted by 1 to 4 substituents selected from alkyl as defined above, alkoxy as defined above, thioalkoxy as defined above, hydroxy, thiol, nitro, halogen, amino,

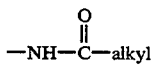

wherein alkyl is as defined above,

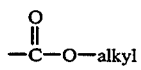

wherein alkyl is as defined above,

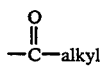

wherein alkyl is as defined above, or aryl.

The term "arylalkyl" means an aromatic radical attached to an alkyl radical wherein aryl and alkyl are as defined above. For Example: benzyl, fluorenylmethyl, and the like.

The term "heteroaryl" means a heteroaromatic radical which is 2-or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, unsubstituted or substituted by 1 to 2 substituents selected from alkyl as defined above, aryl as de fined above, alkoxy as defined above, thioalkoxy as defined above, hydroxy, thiol, nitro, halogen, formyl, amino,

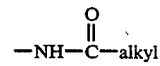

wherein alkyl is as defined above,

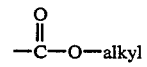

wherein alkyl is as defined above,

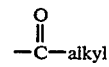

wherein alkyl is as defined above or phenyl.

"Halogen" is fluorine, chlorine, bromine or iodine.

The following table provides a list of abbreviations and definitions thereof used in the present invention.

| Abbreviation* | Amino Acid |
|---|---|
| Asp | Aspartic Acid |
| Bhg | 10,11-Dihydro-5H-dibenzo-[a,d]-(cyclohepten-5-yl)glycine or α-Amino-10,11-dihydro-5H-dibenzo[a,d]cycloheptene-5-acetic acid |
| Ile | Isoleucine |
| Leu | Leucine |
| Trp | Tryptophan |
| Protecting Group | |
| Ac | Acetyl |
| Bzl | Benzyl |
| Boc | tertiary-Butyloxycarbonyl |
| For | Formyl |
| Z | Benzyloxycarbonyl |
| Solvents and Reagents | |
| HOAc | Acetic Acid |
| CH₃CN | Acetonitrile |
| DCM | Dichloromethane |
| DCC | N,N'-Dicyclohexyl-carbodiimide |
| DIPEA | N,N-Diisopropylethylamine |
| DMF | Dimethylformamide |
| HCl | Hydrochloric acid |
| KOH | Potassium hydroxide |
| NaOH | Sodium hydroxide |
| KHMDS | Potassium bis(trimethylsilyl)amide |
| TFA | Trifluoroacetic acid |
| PAM Resin | 4-(Oxymethyl)-phenyl-acetamidomethyl resin |

*If the configuration of the amino acid is other than L(S), the amino acid or abbreviation is preceded by the appropriate configuration D(R) or DL(RS).

The compounds of Formula D-Ia and Formula L-Ib are capable of forming both pharmaceutically acceptable acid addition and/or base salts. The compounds of Formulas D-IIa and L-IIb are capable of forming pharmaceutically acceptable base addition salts. All of these forms are within the scope of the present invention.

Pharmaceutically acceptable acid addition salts of a con,pound of Formula D-Ia and Formula L-Ib include salts derived from nontoxic inorganic acids such as hydrochloric, nitric, phosphoric, sulfuric, hydrobromic, hydriodic, phosphorous and the like, as well as the salts derived from nontoxic organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebecate, fumarate, maleate, mandelate, benzoate, chlorobenzoate, methylbenzoate, nitrobenzoate, phthalate, benzenesulfonate, toluenesulfonate, phenylacetate, citrate, lactate, maleate, tartrate, methanesulfonate and the like. Also contemplated are salts of amino acids such as arginate and the like and gluconate, galacturonate (see, for example, Berge, S. M., et al, "Pharmaceutical Salts," *Journal of Pharmaceutical Science*, 66:1-19 (1977).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free bases for purposes of the present invention.

Pharmaceutically acceptable base addition salts are formed with metals or am/nos such as alkali and alkaline earth metals or organic amines. Examples of metals used as cations are sodium, potassium, magnesium, calcium and the like. Examples of suitable amines are N,N'-dibenzylethylenediamine, chloroprocaine, choline, diethanolamine, ethylenediamine, N-methylglucamine, and procaine (see, for example, Berge, S. M., et al, *Journal of Pharmaceutical Science*, 66:1-19 (1977)).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acids for purposes of the present invention.

A compound of Formulas Ia, IIa, or IIIa may be designated either as D or R and a compound of Formulas Ib, IIb, or IIIb as L or S, respectively.

Certain of the compounds of the present invention can exist in unsolvated forms as well as solrated forms, including hydrated forms. In general, the solvated forms, including hydrated forms, are equivalent to unsolvated forms and are intended to be encompassed within the scope of the present invention.

As previously described, the compounds of Formula D-Ia and Formula L-Ib, are useful as hydrophobic unnatural amino acid replacements to prepare biologically active peptides with enhanced potency and/or metabolic stability.

A preferred compound elf Formula I is one wherein Z is

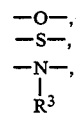

wherein $R^3$ is hydrogen or alkyl,
—$(CH_2)_{\overline{m}}$, wherein m is an integer of 1, 2, 3, or 4, and
—$(CH_2)_{\overline{n}}CH=CH-(CH_2)_{\overline{n}}$, wherein n is zero or an integer of 1;
R is hydrogen;
$R^1$ is hydrogen;
$R^2$ is
hydrogen,
benzyloxycarbonyl,
tertiary-butyloxycarbonyl,
fluorenyloxycarbonyl,
1-adamantyloxycarbonyl, and
2-adamantyloxycarbonyl.

A more preferred compound of Formula I is one wherein
Z is
—O—,
—S—,

wherein $R^3$ hydrogen or alkyl, —$CH_2$—$CH_2$—, and —$CH=CH$—.

Particularly valuable are:
D-α-Amino-9H-xanthene-9-acetic acid;
L-α-Amino-9H-xanthene-9-acetic acid;
D-α-Amino-9H-thioxanthene-9-acetic acid;
L-α-Amino-9H-thioxanthene-9-acetic acid;
DL-α-Amino-9H-thioxanthene-9-acetic acid;
D-α-Amino-10,11-dihydro-5H-dibenzo[a,d]-cycloheptene-5-acetic acid;
L-α-amino-10,11-dihydro-5H-dibenzo[a,d]-cycloheptene-5-acetic acid;
DL-α-Amino-10,11-dihydro-5H-dibenzo[a,d]-cycloheptene-5-acetic acid;
D-α-Amino-5H-dibenzo[a,d]cycloheptene-5-acetic acid;
L-α-Amino-5H-dibenzo[a,d]cycloheptene-5-acetic acid; and
DL-α-Amino-5H-dibenzo[a,d]cycloheptene-5-acetic acid.

SCHEME I
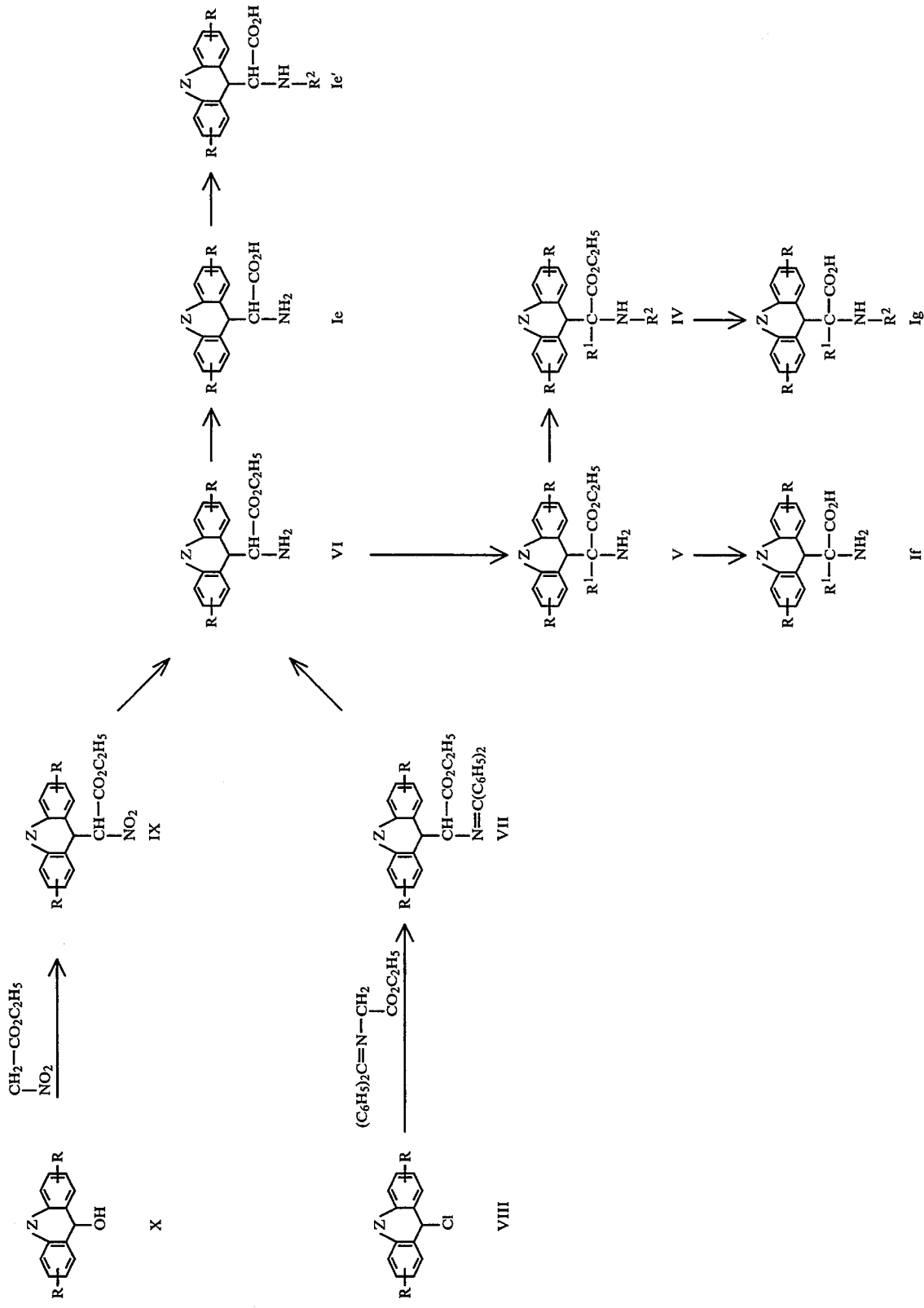

Thus, as outlined in Scheme I, an alcohol of Formula X wherein Z is

—O—,

—S(O)$_n$—, wherein n is zero or an integer of 1 or 2,

wherein R$^3$ is
  hydrogen,
  alkyl,
  alkenyl,
  alkynyl,
  cycloalkyl,
  cycloalkylalkyl,
  aryl,
  heteroaryl,
  fluorenylmethyl,
  CX$_3$,
wherein X is halogen or aryl, —(CH$_2$)$_{\overline{m}}$, wherein m is an integer of 1, 2, 3, or 4, —(CH$_2$)$_{\overline{n}}$CH=CH—(CH$_2$)$_{\overline{n}}$, wherein n is as defined above,

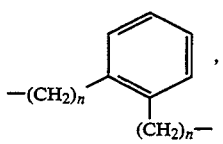

wherein n is as defined above

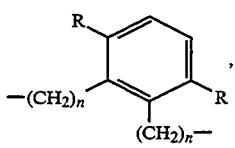

wherein R and n are as defined above,

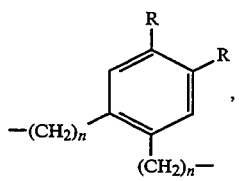

wherein R and n are as defined above; and
R is
  hydrogen,
  methyl,
  trifluoromethyl,
  methoxy,
  hydroxy,
  chloro,
  bromo,
  fluoro,
  iodo,
  2,4-dibromo,
  2,4-dichloro, and
  2,4-difluoro;

is heated with ethyl nitroacetate to about 100° C. to about 110° C. using methodology disclosed by Ryaboi, V. I. and Ginzburg, O. F., *Zhurnal Organischeskoi Khimii* 1: 2069-2071 (1965) to afford a compound of Formula IX wherein Z and R are as defined above. The nitro ester of Formula IX is reduced with hydrogen gas in the presence of a catalyst such as, for example, palladium on carbon in a solvent such as, for example, ethanol and the like and an acid such as, for example, hydrochloric acid to afford a compound of Formula VI. In a compound of Formula IX wherein Z represents an unsaturated moiety the nitro group is selectively reduced with a metal hydride such as, for example, sodium borohydride, in the presence of cobalt chloride and the like and a solvent such as, for example, methanol and the like to afford a compound of Formula VI wherein Z is an unsaturated moiety and R is as defined above.

Alternatively, a compound of Formula VI wherein Z and R are as defined above is obtained by reacting a compound of Formula VIII wherein Z and R are as defined above with a penzophenone imine of ethyl glycinate to afford a compound of Formula VII wherein Z and R are as defined above. A compound of Formula VII is subsequently converted to a compound of Formula VI using the methodology described by O'Donnell, M. J. and Eckrich, T. M., *Tetrahedron Letters*:46-25-4628 (1978); O'Donnell, M. J. and Polt, R. L., *Journal of Organic Chemistry* 47:2663-2666 (1982); and O'Donnell, M. J., et al, *Journal of the American Chemical Society* III: 2353-2355 (1989).

A compound of Formula V wherein Z, R, and R$^1$ are as defined above is obtained from a compound of Formula VI by a conventional alkylation procedure. A compound of Formula IV wherein Z, R, R$^1$, and R$^2$ are as defined above is obtained from a compound of Formula V using a conventional procedure for introduction of a nitrogen protecting group. Compounds of Formulas Ie, If, and Ig wherein Z, R, R$^1$, and R$^2$ are as defined above are obtained respectively from compounds of Formulas VI, V, and IV using a conventional hydrolysis procedure. A compound of Formula Ie$^1$ wherein Z, R, and R$^2$ are as defined above is obtained using the methodology used to prepare a compound of Formula IV from a compound of Formula V.

The second aspect of the present invention is a new, economical, and commercially feasible method for resolving a compound of Formula I into the D and L enantiomers. The process of the present invention in its second aspect is outlined in Scheme II.

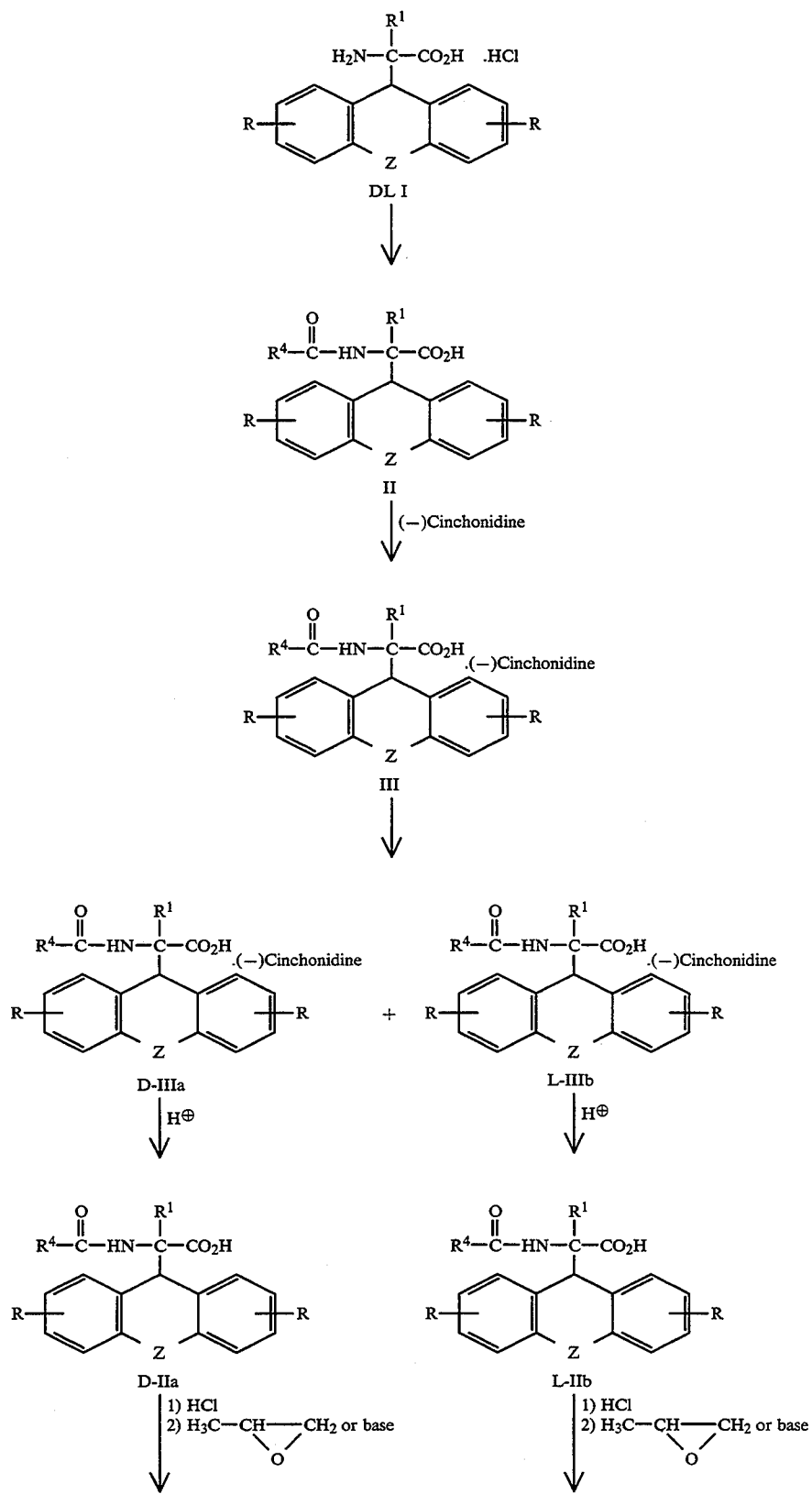
SCHEME II

SCHEME II

-continued

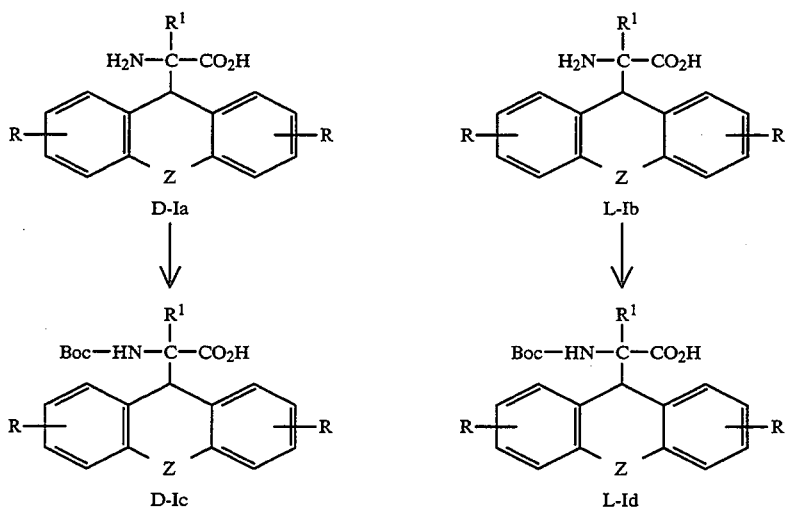

Thus, a compound of Formula DL I, as the amino acid hydrochloride, which is a racemic mixture of isomers is acetylated with a compound of formula

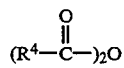

$(R^4-\overset{O}{\underset{\|}{C}}-)_2O$ at about pH 10 to afford a compound of Formula II. A compound of Formula II which is a racemic mixture of isomers is treated with (—)-cinchonidine in a solvent such as, for example, an alcohol, for example, methanol, ethanol, propanol, butanol, and the like, preferably methanol, at about 10° C. to about 100° C. to afford a (—)cinchonidine salt of Formula III. A solution of a compound of Formula III is cooled to about −20° C. to about 25° C. to afford by fractional crystallization a compound of Formula D-IIIa and a con,pound of Formula L-IIIb. Preferably, the reaction is carried out by refluxing the compound of Formula II with (—)cinchonidine in methanol and cooling to about 2° C. to separate the enantiomers by fractional crystallization. A compound of Formula E-IIIa or Formula L-IIIb is treated with an acid such as, for example, hydrochloric acid and the like in a solvent such as, for example, ethyl acetate, dichloromethane, chloroform, toluene, tetrahydrofuran, diethyl ether, and the like at about 0° C. to about 60° C. to afford a compound of Formula D-IIa or Formula L-IIb. Preferably, the reaction is carried out with hydrochloric acid in ethyl acetate at about room temperature. A compound of Formula D-IIa or Formula L-IIb is heated with an acid such as, for example, hydrochloric acid, sulfuric acid, para toluenesulfonic acid, and the like to afford a compound of Formula D-Ia or Formula L-Ib as an acid addition salt. Preferably, the reaction is carried out by refluxing in hydrochloric acid.

The acid addition salt of a compound of Formula D-Ia or Formula L-Ib is treated with a base such as, for example, ammonium hydroxide, to afford a compound of Formula D-Ia or Formula L-Ib, respectively, as the free amino acid. Alternatively, the acid addition salt of a compound of Formula D-Ia or Formula L-Ib may be treated with propylene oxide using the methodology of Schollkopf, U. , et al, Synthesis, pp. 966–969 (1981) to afford a compound of Formula D-Ia or Formula L-Ib, respectively, as the free amino acid.

The N-α-tertiary-butyloxycarbonyl (Boc) derivatives (Formulas D-Ic and L-Id) of a compound of Formula D-Ia or Formula L-Ib are prepared from a compound of Formula D-Ia or Formula L-Ib according to the methodology used to prepare Boc DL-3,3-diphenylalanine disclosed in U.S. Pat. No. 4,766,109. The Boc derivatives may also be prepared by other conventional methodology known in the art. Other N-protected derivatives of a compound of Formula I wherein $R^2$ is as defined above, excluding $R^2$ is hydrogen may be prepared from a compound of Formula D-Ia or L-Ib using conventional methodology.

The configuration of a compound of Formula Ia or Formula Ib is determined by a chiral synthesis of D- and L-Bhg using methodology disclosed by Evans, D. A., et al, Journal of the American Chemical Society 112: 4011–4030 (1990) and Evans, D. A. , et al, Journal of the American Chemical Society 111:1063–1072 (1989) as outlined in Scheme III and Scheme IV.

Thus, as outlined in Scheme III, dibenzosuberol (XVI) is heated with malonic acid to about 160° C. to afford 10,11-dihydro-5H-dibenzo[a,d]cycloheptene-5-acetic acid (XV). A solution of the acid (XV) in a solvent such as, for example, ethylene glycol dimethyl ether and the like in the presence of a base such as, for example, N,N-diisopropylethylamine and the like is reacted with pivaloyl chloride to afford the mixed anhydride (XIV) in situ.

Sodium azide is added to a solution of 2,4,6-triisopropylbenzenesulfonyl chloride (XVIII) in a solvent such as, for example, ethanol and the like to afford the azide (XVII). (1S,2R)-Norephedrine (XX) is treated with diethyl carbonate in the presence of a base such as, for example, potassium carbonate, to afford (4R, 5S)-4-methyl-5-phenyl-2-oxazolidinone (XIX). A solution of the mixed anhydride (XIV) in a solvent such as, for example, ethylene glycol dimethyl ether and the like, is added to the lithiated oxazolidinone solution in a solvent such as, for example, tetrahydrofuran and the like (the lithiated oxazolidinone is prepared by treating a compound of Formula XIX with n-butyl lithium) to afford the acyloxazolidinone (XIII). Deprotonation of XIII by treating with potassium his (trimethylsilyl)

amide (KHMDS) in a solvent such as, for example, tetrahydrofuran and the like, followed by the addition of a solution of the azide (XVII) in a solvent such as, for example, tetrahydrofuran and the like and rapid quenching with an acid such as, for example, acetic acid and the like to afford the azido oxazolidinone (XII). The azido oxazolidinone (XII) is hydrolyzed with lithium hydroxide in hydrogen peroxide to afford the azido acid (XI). Treatment of the azido acid (XI) with hydrogen in the presence of a catalyst such as, for example, palladium on carbon and the like, in tetrahydrofuran and 1N hydrochloric acid affords (R)-α-amino-10,11-dihydro-5H-dibenzo[a,d]cyclo-heptene-5-acetic acid hydrochloride (R-Ih).

(S)-α-Amino-10,11-dihydro-5H-dibenzo[a,d]cycloheptene-5-acetic acid hydrochloride ( S-Ii) is prepared using the same methodology as used to prepare (R)-α-amino-10,11-dihydro-5H-dibenzo[a,d]cycloheptene-5-acetic acid hydrochloride by substituting (4S,5R)-4-methyl-5-phenyl-2-oxazolidinone (XIXa) for (4R,5S )-4-methyl-5-phenyl-2-oxazolidinone (XIX) as outlined in Scheme IV.

The synthesis of D-α-amino-5H-dibenzo[a,d]cycloheptene-5-acetic acid (R-Ij) is outlined in Scheme V and follows a procedure similar to the one outlined in Scheme III. The reduction of the azido acid (XXI) is best achieved chemically using such as, for example, stannous chloride in a solvent such as methanol in order to avoid the reduction of the double bond which could occur under catalytic hydrogenation conditions.

The L-α-amino-5H-dibenzo[a,d]cycloheptene-5-acetic acid (S-Ik) is prepared by the same methodology as outlined in Scheme V, substituting (4S,5R)-4-methyl-5-phenyl-2-oxazolidinone (XIXa) for (4R,5S) -4-methyl-5-phenyl-2-oxazolidinone (XIX) as outlined in Scheme VI.

The following nonlimiting examples are illustrative to show the present process, the preparation of starting materials, and the use of α-amino-10,11-dihydro-5H-dibenzo[a,d]cycloheptene-5-acetic acid obtained by the present process to prepare Acetyl-D-Bhg-Leu-Asp-Ile-Ile-Trp, an antagonist of endothelin useful in the treatment of hypertension, myocardial infarction, metabolic, endocrinological and neurological disorders, congestive heart failure, endotoxic shock, subarachnoid hemorrhage, arrhythmias, asthma, acute renal failure, preeclampsia, and diabetes which is disclosed in a copending United States Patent Application Serial filed simultaneously with the present application.

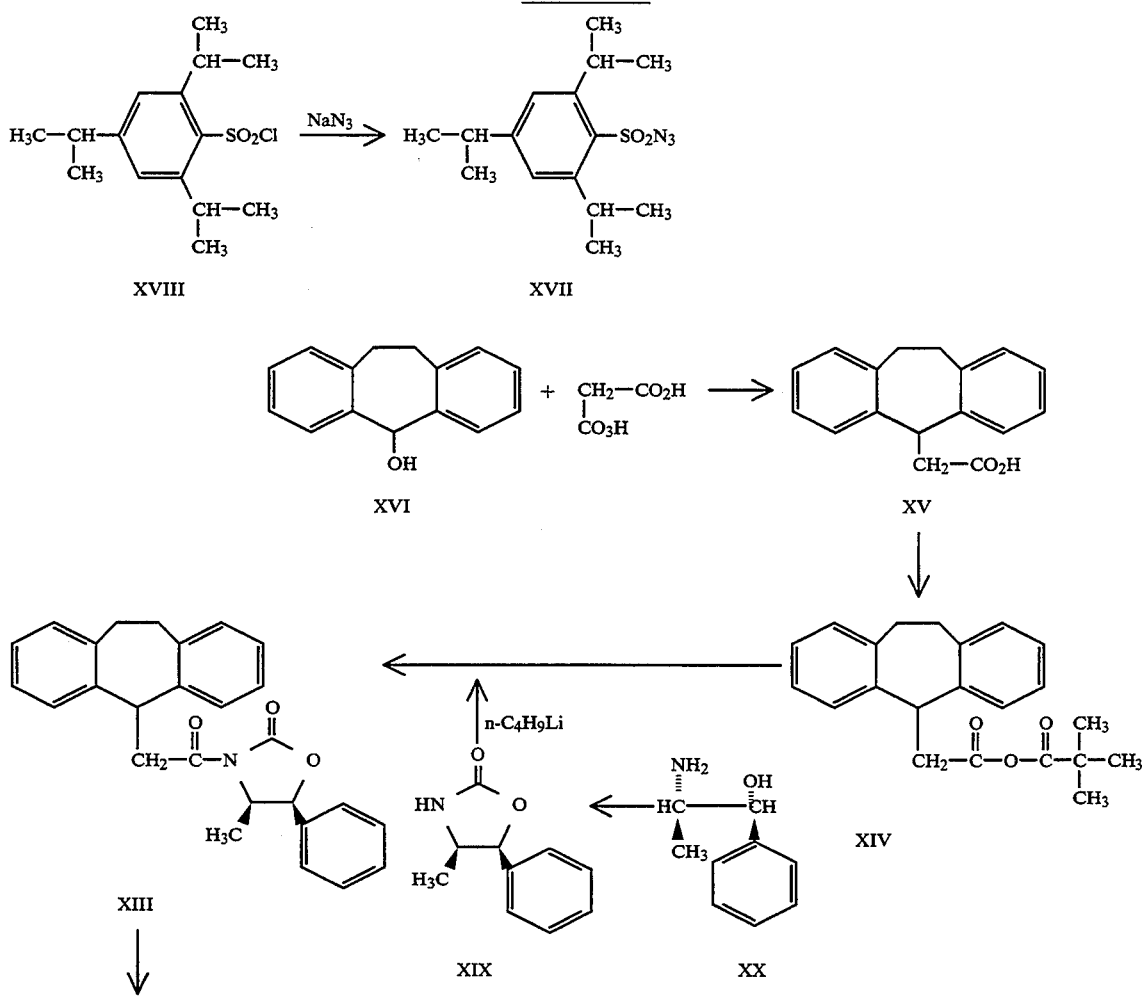

-continued
SCHEME III
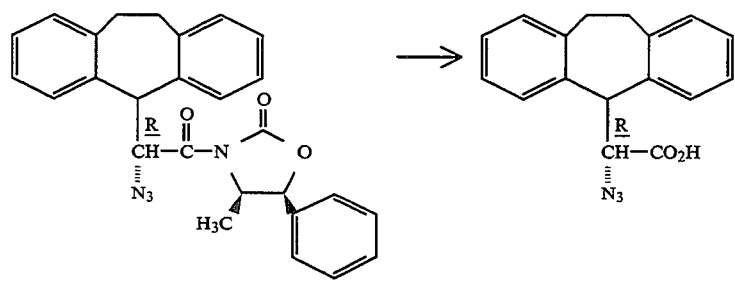
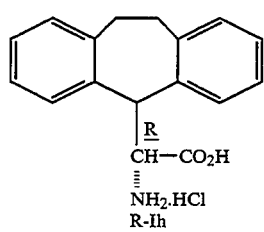
SCHEME IV
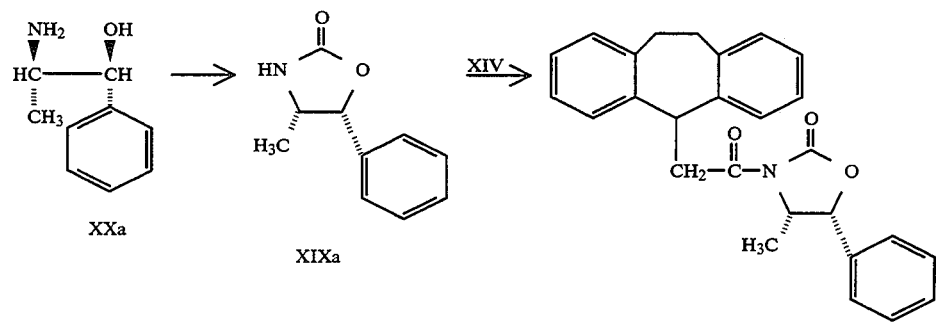
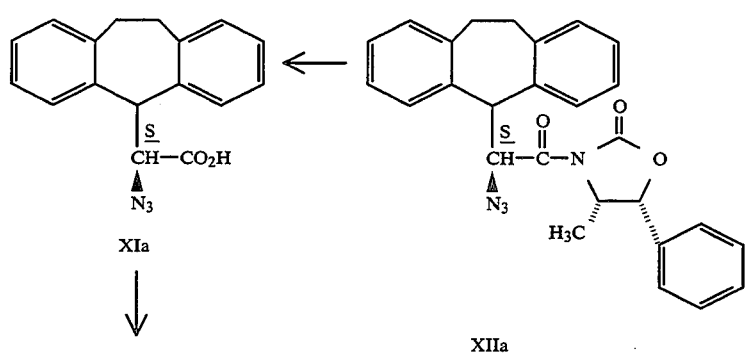

SCHEME IV
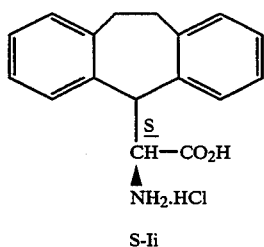
SCHEME V
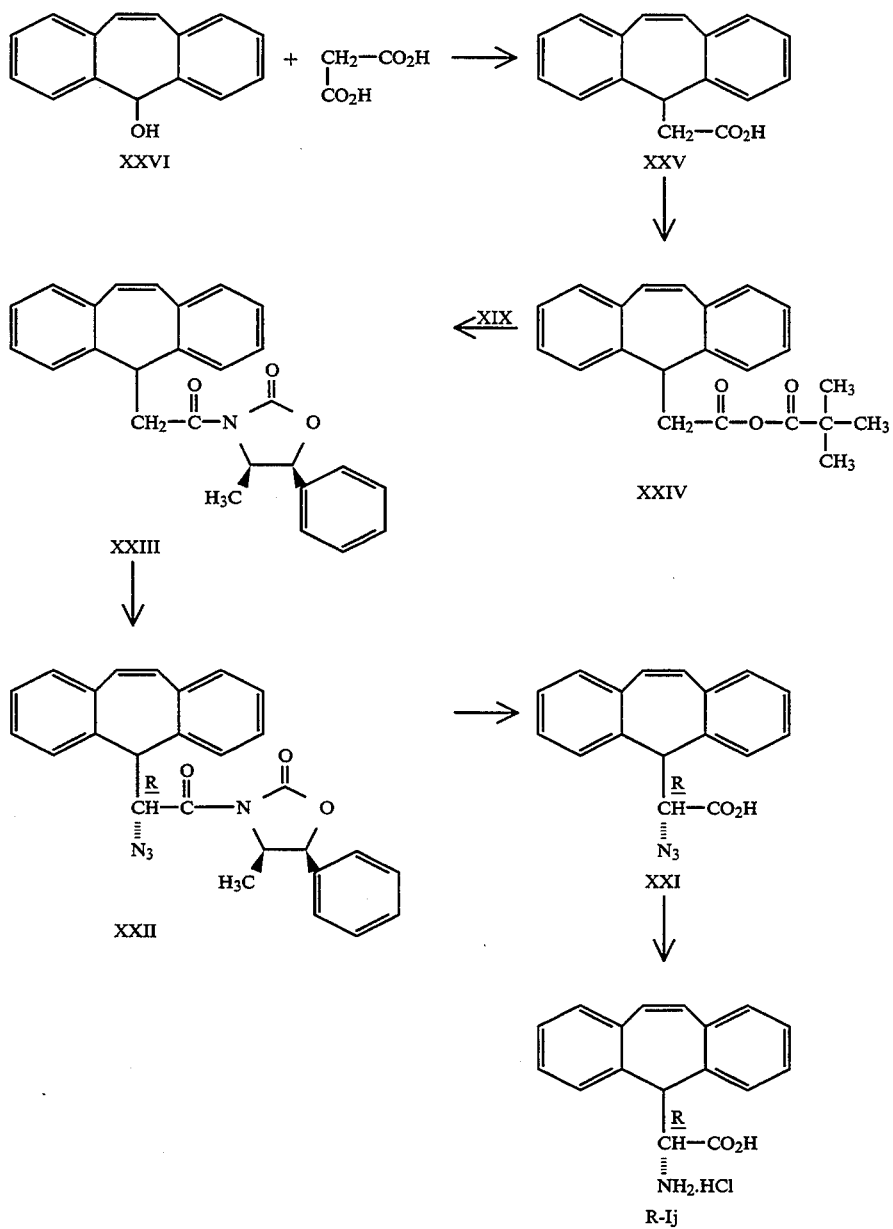

SCHEME VI

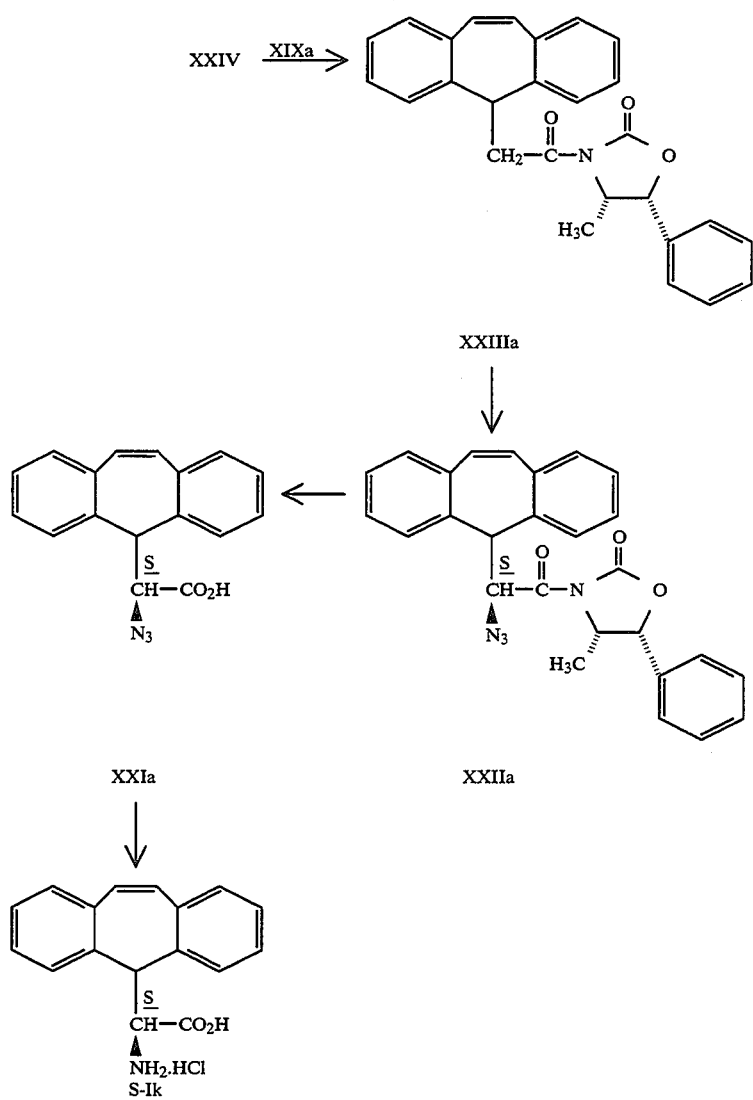

EXAMPLE 1

α-Amino-9H-xanthene-9-acetic acid

Step A: Preparation of Ethyl α-nitro-9H-xanthene-9-acetate

9-Hydroxyxanthene (9.9 g, 50 mmol) and ethyl nitroacetate (6.1 mL, 55 mol) are mixed and heated at 100° C. (oil bath) for 1.5 hours. After cooling, a waxy mixture is suspended in 40 mL of absolute alcohol and 40 mL of 1.25M of ethanolic potassium hydroxide solution is added. The solution is stirred for 45 minutes at room temperature and ethanol is stripped off. The remaining solid is suspended in water and extracted with diethyl ether. The aqueous portion is acidified with 85% phosphoric acid to pH 2 to 3 to give a white suspension which is cooled overnight. The precipitate is collected by filtration and dried in a vacuum oven at 50° C. This gives 9.18 g of the title compound as a white solid; mp 89°–91° C.

Step B: Preparation of Ethyl α-amino-9H-xanthene-9-acetate hydrochloride

Ethyl α-nitro-9H-xanthene-9-acetate (7.5 g, 24 mmol) is dissolved in 150 mL of ethanol and 2 mL of concentrated hydrochloric acid and hydrogenated over 1.0 g of 20% palladium on carbon (53 hours, 51 pounds per square inch (psi)). The filtered solution is stripped or solvent and washed with dichloromethane. This gives 4.83 g of the title compound. An additional crop, 0.61 g is obtained after cooling the dichloromethane wash. The crops are combined and used in the next step.

Step C: Preparation of α-Amino-9H-xanthene-9-acetic acid, hydrochloride

Ethyl α-amino-9H-xanthene-9-acetate hydrochloride (5.33 g, 17 mmol) is combined with 45 mL of absolute ethanol and 27 mL of 1.25M ethanolic potassium hydroxide solution (2 equivalents). The progress of the reaction is monitored by thin layer chromatography (TLC), silica gel ($SiO_2$), hexane:2-propanol/3:7 with 1% of acetic acid. After 13 hours and an additional two equivalents of the potassium hydroxide solution (in three portions) most of the starting material is consumed. Ethanol is stripped off, the residue is taken up in 100 mL of water, and extracted with diethyl ether. The aqueous portion is acidified with 0.5N hydrochloric acid (∼100 mL) to pH 2 and cooled overnight. A white precipitate is collected by filtration, washed with cold water, diethyl ether, and dried at 50° C./10 mm Hg. This provides 3.18 g of the title compound; mp 264°–269° C. (dec).

Step D: Preparation of α-Amino-9H-xanthene-9-acetic acid

α-Amino-9H-xanthene-9-acetic acid hydrochloride is dissolved in water and the pH of the solution is adjusted with dilute ammonium hydroxide solution to pH 7. The precipitate is collected by filtration, washed with water, boiled with water for a short time, cooled to room temperature, and collected to afford the title compound.

EXAMPLE 2

α-Amino-9H-thioxanthene-9-acetic acid

Step A: Preparation of 9-Hydroxythioxanthene (Price, L. L., et al, *Journal of the American Chemical Society* 85:2278 (1963))

Thioxanthene-9-one (10 g, 47 mmol) is dissolved in 150 mL of methanol, cooled with an ice bath, and 5.0 g (132 mmol) of sodium borohydride is added in portions. The ice bath is removed and the mixture is allowed to stir at room temperature for an additional 15 minutes until the reaction is completed. Methanol is removed under vacuum and the residual solid washed with diethyl ether. This gives 9.58 g of the title compound which is used in the next step without further purification.

Step B: Preparation of Ethyl α-nitro-9H-thioxanthene-9-acetate

Crude 9-hydroxythioxanthene (9.58 g, 45 mmol) is mixed with ethyl nitroacetate (5.5 mL, 49 mmol) and heated at 100° C. for 1 hour. TLC ($SiO_2$, hexane:2-propanol/3:1) after 45 minutes shows no starting material. The cooled reaction mixture is treated with 100 mL of ethanol and 39 mL of 1.25M ethanolic potassium hydroxide solution. Ethanol is stripped and the residue taken up in water and extracted with diethyl ether. The aqueous layer is acidified to pH 2 to 3 with 85% phosphoric acid solution and refrigerated overnight. A crystalline solid is collected by filtration and dried at 50° C./10 mm Hg. A total of 8.4 g of the title compound is collected in three crops; mp 111°–115° C.

Step C: Preparation of Ethyl α-amino-9H-thioxanthene-9-acetate hydrochloride

Ethyl α-nitro-9H-thioxanthene-9-acetate (4.4 g, 13.4 mmol) is hydrogenated in 200 mL of ethanol and 13.5 mL of concentrated hydrochloric acid with 1.0 g of 20% palladium on carbon (51 psi, 28 hours). The filtered solution is stripped of solvent and the residual solid washed with dichloromethane, dried at 45° C./2 mm Hg. This gives 3.66 g of the title compound; mp 238°–240° C. An additional crop (0.41 g) is obtained after cooling the mother liquor; mp 233°–236° C.

Step D: Preparation of α-Amino-9H-thioxanthene-9-acetic acid, hydrochloride

Ethyl α-amino-9H-thioxanthene-9-acetate hydrochloride (3.5 g, 10 mmol) is dissolved in 30 mL of absolute ethanol and 33 mL of 1.25M ethanolic potassium hydroxide solution (4 equivalents) is added. The reaction mixture is stirred at room temperature for 22 hours when TLC ($SiO_2$, hexane: 2-propanol/3:1) shows no starting material. Ethanol is stripped under vacuum and the residue taken up in 75 mL of water and extracted with diethyl ether. The aqueous solution is acidified with 1N hydrochloric acid to pH 7 and a precipitate is collected by filtration, washed with water, dried at 45° C./2 mm Hg over phosphorous pentoxide ($P_2O_5$). This gives 1.65 g of the title compound; mp 244°–246° C. The mother liquor is concentrated, cooled at +3° C. to furnish the second crop (0.57 g) of the title compound as a hydrochloride-free base mixture. The above solids are combined in 50 mL of water and treated with 1N hydrochloric acid to pH 1. The mixture is stripped to dryness under vacuum and the residue dried at 50° C./2 mm Hg to give the title compound; mp 269°–273° C. (dec).

Step E: Preparation of α-Amino-9H-thioxanthene-9-acetic acid

Using the methodology of Example 1 (Step D), the title compound is prepared from α-amino-9H-thioxanthene-9-acetic acid hydrochloride.

EXAMPLE 3

α-Amino-10,11-dihydro-5H-dibenzo[a,d]cycloheptene-5-acetic acid

Method A

Step A: Preparation of Ethyl 5-[(diphenylmethylene)-amino]-10,11,dihydro-5H-dibenzo[a,d]cycloheptene-5-acetate Ethyl N- (diphenylmethylene) glycinate (12 g, 45 mmol) and 5-chlorodibenzosuberane (12.32 g, 54 mmol) are dissolved in 250 mL of dichloromethane, tetrabutylammonium bromide (17.6 g, 55 mmol) and 47 mL of 50% sodium hydroxide solution are added and the mixture is mechanically stirred at room temperature for 4 hours. Then it is diluted with 75 mL of dichloromethane and water and the layers are separated. The organic layer is washed with water, dried over magnesium sulfate, filtered, and stripped under vacuum to give a brown-orange oil. The oil is taken up in 250 mL of diethyl ether and 100 mL of water. The diethyl ether solution is additionally washed with water, dried (magnesium sulfate), and stripped to give a clear red-orange sticky oil residue (~21 g) which is used in the next step without purification.

Step B: Preparation of α-Amino-10,11-dihydro-5H-dibenzo[a,d]cycloheptene-5-acetic acid, hydrochloride The crude ethyl 5-[(diphenylmethylene) amino]-10,11-dihydro-5H-dibenzo[a,d]cycloheptene-5-acetate is mixed with 250 mL of 6N hydrochloric acid solution and heated at reflux for 2 hours. After cooling to room temperature a solid is collected by filtration, washed with water and diethyl ether, air dried, then dried at 50° C./2 mm Hg. This provides 6.43 g of the title compound; mp >280 ° C.

Step C: Preparation of α-Amino-10,11-dihydro-5H-dibenzo[a,d]cycloheptene-5- acetic acid Using the methodology of Example 1 (Step D), the title compound is prepared from 2-amino-10,11-dihydro-5H-dibenzo[a,d]cycloheptene-5-yl acetic acid hydrochloride.

Method B

Step A: Preparation of α-Amino-10,11-dihydro-5H-dibenzo[a,d]cycloheptene-5-acetate hydrochloride Ethyl α-nitro-5H-dibenzo[a,d]cycloheptene-5-acetate (13 g, 40 mmol) (Example 4, Step A) is dissolved in 150 mL of ethanol, 40 mL of water, and 3.5 mL of concentrated hydrochloric acid and hydrogenated with 2.0 g of 20% palladium on carbon (52 psi, 30 hours). The filtered solution is stripped and a white solid washed with diethyl ether, dried at 50° C./2 mm Hg. The crude product is used as is in the next step.

Step B: Preparation of α-Amino-10,11-dihydro-5H-dibenzo [a,d]cycloheptene-5-acetic acid, hydrochloride Ethyl α-amino-10,11-dihydro-5H-dibenzo[a,d]cycloheptene-5-acetate hydrochloride (13 g, 39 mmol) is stirred with 400 mL of 1M ethanolic potassium hydroxide solution at room temperature overnight. Ethanol is stripped and the solid taken up in water, extracted with diethyl ether, and acidified with 1N hydrochloric acid to pH 1. A precipitate is collected by filtration, washed with diethyl ether, dried at 50° C./2 mm Hg to furnish 8.81 g of the title compound; mp >285° C.

Step C: Preparation of α-Amino-10,11-dihydro-5H-dibenzo [a,d]cycloheptene-5-acetic acid Using the methodology of Example 1 (Step D) the title compound is prepared from 2-amino-10,11-dihydro-5H-dibenzo[a,d]cycloheptene-5-yl-acetic acid, hydrochloride.

EXAMPLE 4

α-Amino-5H-dibenzo[a,d]cycloheptene-5-acetic acid

Step A: Preparation of Ethyl α-nitro-5H-dibenzo[a,d]cycloheptene-5-acetate

Dibenzosuberenol (42 g, 0.2 mol) is combined with ethyl nitroacetate (25 mL, 0.23 mol) and the mixture is heated at 120° C. (oil bath) until melted and then kept at 110° C. for 2.5 hours. The oil bath is removed and the cooled reaction mixture is dissolved in 50 mL of methanol and taken up into 350 mL of boiling diethyl ether. The dark solution is treated with charcoal, filtered, and cooled overnight. A precipitate is collected by filtration, washed with hexane, diethyl ether, dried under vacuum at room temperature to give 26.7 g of the title compound; mp 101°–103° C.

Step B: Preparation of Ethyl α-amino-5H-dibenzo[a,d]cycloheptene-5-acetate, hydrochloride Ethyl α-nitro-5H-dibenzo[a,d]cycloheptene-5-acetate (1 g, 3.4 mmol) and cobalt chloride- 6H2O (1.6 g, 6.8 mmol) are dissolved in 20 mL of absolute ethanol, and sodium borohydride (1.28 g, 34 mmol) is added in portions over 20 minutes. An additional 15 mL of ethanol is used to wash all sodium borohydride into solution and the stirring is continued for 1 hour. Thirty mL of 3N hydrochloric acid is added and the solution is stirred until it turns purple. The insoluble part of the reaction mixture is filtered and ethanol stripped off on a rotary evaporator. The aqueous solution is filtered to give a blue-white solid which is washed exhaustively with 6N hydrochloric acid, and then finally with diethyl ether. The white solid is dried at 50° C./2 mm Hg to give 0.65 g of the title compound; mp 253°–256° C. (dec).

Step C: Preparation of α-Amino-5H-dibenzo[a,d]cycloheptene-5-acetic acid, hydrochloride Ethyl α-amino-5H-dibenzo[a,d]cycloheptene-5-acetate, hydrochloride (0.21 g, 0.6 mmol) dissolved in 10 mL of absolute ethanol is stirred with 3 mL of 1.25M ethanolic potassium hydroxide solution until TLC (SiO2, hexane: 2-propanol/3: 1) shows no starting material (2 hours). The solvent is stripped and a residual solid is taken up in water and extracted with dichloromethane. The aqueous layer is acidified with 6N hydrochloric acid to pH 1 and stripped to dryness. The residue is treated with 5 mL of boiling water, cooled to room temperature, then refrigerated overnight. A solid is collected, washed with diethyl ether (0.05 g); mp 225° C. (dec).

Step D: Preparation of α-Amino-5H-dibenzo[a,d]cycloheptene-5-acetic acid

Using the methodology of Example 1 (Step D) the title compound is prepared from α-amino-5H-dibenzo[a,d]cycloheptene-5-acetic acid, hydrochloride.

EXAMPLE 5

D-α-Amino-10,11-dihydro-5H-dibenzo[a,d]cycloheptene-5-acetic acid

Step A: Preparation of α-Acetylamino-10,11-dihydro-5H-dibenzo[a,d]cycloheptene-5-acetic acid α-Amino-10,11-dihydro-5H-dibenzo[a,d]cycloheptene-5-acetic acid, hydrochloride (5.0 g, 16.5 mmol) is dissolved in 1N sodium hydroxide (70 mL) and 50 mL of water, cooled in an ice bath, and treated with acetic anhydride (2.3 mL, 25 mmol) keeping pH at 10 to 10.5. The mixture is stirred for an additional 20 minutes, then the pH is adjusted to 3 to 4 with concentrated hydrochloric acid. A precipitate is collected, washed with water, diethyl ether, and dried in a vacuum oven (50° C./10 mm Hg). The dried solid is recrystallized from ethyl acetate-hexane to give 2.41 g of the title compound; mp 220°–223° C.

Step B: Preparation of D-α-Acetylamino-10,11-dihydro-5H-dibenzo[a,d]cycloheptene-5-acetic acid, cinchonidinium salt D-α-Acetylamino-10,11-dihydro-5H-dibenzo[a,d]cycloheptene-5-acetic acid (2.25 g, 7.3 mmol) is dissolved in 10 mL of methanol and combined with a solution of (−)-cinchonidine (2.36 g, 8 mmol) in 15 mL of boiling methanol. The mixture is allowed to cool to room temperature and placed in a refrigerator (+2° C.). Two crops of the precipitate (0.77 g, $[\alpha]_D = -38°$ and 0.27 g, $[\alpha]_D = -41°$ are combined and used in the preparation of the D-enantiomer.

The mother liquor is stripped of solvent to give a residue which is recrystallized from methanol. The cinchonidinium salt, 2.4 g, $[\alpha]_D = -74.5°$, obtained after stripping the mother liquor is used in the preparation of the L-enantiomer.

Step C: Preparation of D-α-Acetylamino-10,11-dihydro-5H-dibenzo[a,d]cycloheptene-5-acetic acid D-α-Acetylamino-10,11-dihydro-5H-dibenzo[a,d]cycloheptene-5-acetic acid, cinchonidinium salt (0.32 g, 0.5 mmol) is combined with 6 mL of ethyl acetate and 2 mL of 1N hydrochloric acid and stirred at room temperature for 1 hour. The organic layer is separated, washed with water, brine, dried (magnesium sulfate). The filtered solution is stripped of solvent to give 0.13 g of the title compound which is used as is in the next step.

Step D: Preparation of D-α-Amino-10,11-dihydro-5H-dibenzo[a,d]cycloheptene-5-acetic acid, hydrochloride 0.13 g of D-α-acetylamino-10,11-dihydro-5H-dibenzo [a,d]cycloheptene-5-acetic acid is heated at reflux with 10 mL of 6N hydrochloric acid for 6 hours. After cooling, a precipitate is collected by filtration, washed with diethyl ether, dried in a vacuum oven (50° C./10 mm Hg) to give 0.09 g of the title compound, $[\alpha]_D = -47° \pm 1°$ (1% in methanol), mp $\geq 280°$ C.

Step E: Preparation of D-α-Amino-10,11-dihydro-5H-dibenzo[a,d]cycloheptene-5-acetic acid Using the methodology of Example 1 (Step D) the title compound is prepared from D-α-amino-10,11-dihydro-5H-dibenzo[a,d]cycloheptene-5-acetic acid, hydrochloride.

EXAMPLE 6

L-α-Amino-10,11-dihydro-5H-dibenzo[a,d]cycloheptene-5-acetic acid

Step A: Preparation of L-α-Acetylamino-10,11-dihydro-5H-dibenzo[a,d]cycloheptene-5-acetic acid The L-α-Acetylamino-10,11-dihydro-5H-dibenzo[a,d]cycloheptene-5-acetic acid, cinchonidinium salt (2 g, 3.3 mmol) from Example 5 is combined with 45 mL of ethyl acetate and 16 mL of 1N hydrochloric acid and the mixture is stirred at room temperature for 1 hour. After work-up as described in Example 5, 0.27 g of a solid is collected by filtration. Stripping of the mother liquor furnished 0.77 g of the title compound which is used as is in the preparation of L-enantiomer.

Step B: Preparation of Enriched L-α-Amino-10,11-dihydro-5H-dibenzo[a,d]cycloheptene-5-acetic acid, hydrochloride 0.75 g of L-α-acetylamino-10,11-dihydro-5H-dibenzo[a,d]cycloheptene-5-acetic acid is combined with 30 mL of 6N hydrochloric acid and the mixture is heated at reflux for 6 hours. The cooled reaction mixture is refrigerated overnight. A solid is collected by filtration, washed with diethyl ether, dried (50° C./10 mm Hg) to give 0.57 g of the title compound, $[\alpha]_D + 36°$ (1% in methanol).

Step C: Preparation of L-α-amino-10,11-dihydro-5H-dibenzo[a,d]cycloheptene-5-acetic acid Using the methodology of Example 1 (Step D) the title compound is prepared from L-α-amino-10,11-dihydro-5H-dibenzo[a,d]cycloheptene-5-acetic acid, hydrochloride.

EXAMPLE 7

(R)-α-amino-10,11-dihydro-5H-dibenzo[a,d]cycloheptene-5-acetic acid

Step A: Preparation of 10,11-Dihydro-5H-dibenzo[a,d]cycloheptene-5-acetic acid

A round-bottom flask, equipped with a distillation apparatus, is charged with dibenzosuberol (25.0 g, 0.119 mol) and malonic acid (61.9 g, 0,595 mol). The mixture is heated in an 160° C. oil bath. The solids melt. Gas bubbles form and water and acetic acid are distilled through the condenser. After 30 minutes, the mixture is cooled to room temperature and dissolved in ethyl acetate. The organic solution is washed with brine and dried (magnesium sulfate). The solvent is removed in vacuo to give an off-white solid, which is recrystallized from hexane-ethyl acetate/1:1 to yield the title compound as white crystals, 28.8 g; mp 164°–165° C.

Step B: Preparation of (4R-cis)-3-[(10,11-dihydro-5H-dibenzo[a,d]cycloheptene-5-yl)acetyl]-4-methyl-5-phenyl-2-oxazolidinone A solution of 10,11-dihydro-5H-dibenzo[a,d]cycloheptene-5-acetic acid (12.0 g, 47.56 mmol) in anhydrous ethylene glycol dimethyl ether (DME) (60 mL) is cooled to −20° C. under nitrogen, and freshly distilled diisopropylethyl amine (9.9 mL, 57.07 mmol) is added, followed by slow addition of pivaloyl chloride (6.4 mL, 52.32 mmol). The resulting milky slurry is stirred at −20° C. for 30 minutes. The white solid is filtered, washed with DME (10 mL). The filtrate of the mixed anhydride is cooled to −78° C. under a nitrogen atmosphere. In a separate flask, (4R)-methyl-(5S)-phenyl-2-oxazolidinone (9.3 g, 52.32 mmol) (Example A) is dissolved in freshly distilled tetrahydrofuran (100 mL) and cooled to −78° C. under argon. Several crystals of triphenylmethane is added as an indicator. To this solution is added n-butyllithium (34.3 mL, 54.93 mmol, 1.6M solution in hexane). The red solution is stirred at −78° C. for 5 minutes, and the solution of the mixed anhydride, prepared as described above, is added via cannula. The resulting light yellow solution is stirred at −78° C. for 15 minutes, and then warmed to room temperature over 2 hours. The reaction is quenched by addition of aqueous ammonium chloride. The tetrahydrofuran is removed in vacuo and the residue is extracted with dichloromethane (3×200 mL). The organic extracts are combined and washed successively with aqueous sodium bicarbonate solution, brine, dried (magnesium sulfate), and concentrated in vacuo. The resulting yellow solid is recrystallized from hexane-ethyl acetate/4:1 to give the title compound as a white solid, 16.2 g; mp 133°–134° C.; $[\alpha]_D = +14.0°$ (c=1.0, chloroform).

Step C: Preparation of (4R-[3(R*),4α,5α]]-3-[Azido-(10,11-dihydro-5H-dibenzo[a,d]cycloheptene-5-yl) acetyl]-4-methyl-5-phenyl-2-oxazolidinone To a solution of (4R-cis)-3-[(10,11-dihydro-5H-dibenzo [a,d]cycloheptene-5-yl)acetyl]-4-methyl-5-phenyl-2-oxazolidinone (15.6 g, 37.9 mmol) in freshly distilled tetrahydrofuran (505 mL) , at −78° C., under argon, is added potassium his (trimethylsilyl) amide (83.4 mL, 41.7 mmol, 0.5M solution in toluene) dropwise. The yellow solution is stirred at −78° C. for 1 hour, and a solution of 2,4,6-triisopropyl-benzene sulfonylazide (Example B) (15.3 g, 49.3 mmol) in dry tetrahydrofuran (10 mL) is added. After 10 minutes at −78° C., acetic acid (9.1 mL, 159.2 mmol) is added quickly and the mixture is heated on a steam bath immediately to 30° C., and then stirred at room temperature for 2 hours. The mixture turns milky. The tetrahydrofuran is removed in vacuo, and the resulting off-white paste is dissolved in dichloromethane (600 mL), washed successively with half saturated brine and half saturated sodium bicarbonate solution, and dried (magnesium sulfate). Evaporation of solvent in vacuo gives an off-white solid, which is recrystallized from hexane-ethyl acetate/1.5:1, to give the title compound as white crystals, 14.3 g; mp 171° C.; $[\alpha]_D = -178.5°$ (C=1.0, chloroform).

Step D: Preparation of (R)-α-Azido-10,11-dihydro-5H-dibenzo[a,d]cycloheptene-5-acetic acid To a solution of [4R-[3(R*),4α, 5α]]-3-[azido-(10,11-dihydro-5H-dibenzo[a,d]cycloheptene-5-yl )-acetyl ]-4-methyl-5-phenyl-2-oxazolidinone (13.7 g, 30.27 mmol) in 4:1 tetrahydrofuran-water (300 mL) at 0 ° C., is added a solution of lithium hydroxide (2.5 g, 60.54 mmol) in hydrogen peroxide (17.2 mL, 151.35 mmol, 30% aqueous) dropwise under nitrogen. The milky mixture is stirred at 0 ° C. for 1 hour. Aqueous sodium sulfite (50 mL) is added. The bulk of the tetrahydrofuran is evaporated in vacuo. The aqueous solution is cooled in an ice bath and acidified with 6N hydrochloric acid to pH 1. The white solid is extracted with dichloromethane (5X) and dried (magnesium sulfate). Evaporation of solvent in vacuo gives a yellow oil, which is purified by flash chromatography (silica gel, hexane-ethyl acetate-acetic acid/100:50:1) to yield the title compound as a white solid, 8.3 g; mp 101°–102° C., $[\alpha]_D = 38.7°$ (c=1.0, methanol). The chiral auxiliary ((4R)-methyl-(5S)-phenyl-2-oxazolidinone) is recovered as a white solid, 5.2 g; mp 120°–122 ° C.

Step E: Preparation of (R)-α-Amino-10,11-dihydro-5H-dibenzo[a,d]cycloheptene-5-acetic acid, hydrochloride To a solution of (R)-α-azido-10,11-dihydro-5H-dibenzo[a,d]cycloheptene-5-acetic acid (3.5 g, 1.9 mmol) in tetrahydrofuran (75 mL), water (10 mL), and concentrated hydrochloric acid (1 mL) is added palladium on carbon (0.5 g, 20%). The mixture is shaken under 52 pounds per square inch (psi) of hydrogen at 25° C. for 6 hours. Solid is filtered. The filtrate is concentrated in vacuo to give a light green solid, which is recrystallized in 3N hydrochloric acid (with activated charcoal) to give the title compound as a white solid, 2.84 g; mp 313°–314° C. (dec), $[\alpha]_D = 47.6°$ (c = 1.0, methanol).

Step F: Preparation of (R)-α-Amino-10,11-dihydro-5H-dibenzo[a,d]cycloheptene-5-acetic acid Using the methodology of Example 1 (Step D) the title compound is prepared from (R)-α-amino-10,11-dihydro-5H-dibenzo[a,d]cycloheptene-5-acetic acid, hydrochloride.

EXAMPLE 8

N-Tertiary-butyloxycarbonyl-D-α-amino-10,11-dihydro-5H-dibenzo[a,d]cycloheptene-5-acetic acid To a clear colorless solution of (R)-α-amino-10,11-dihydro-5H-dibenzo[a,d]cycloheptene-5-acetic acid (Example 7), as the hydrochloride (0.5 g, 1.65 mmol) in methanol (15 mL) is added diisopropylethylamine followed by ditertiary butyl dicarbonate. The clear solution is stirred at room temperature overnight (18 hours) and concentrated in vacuo. The resulting colorless oil is flash chromatographed (silica gel, hexane-ethyl acetate:100:50:1) to afford 0.58 g of the title compound as a white solid; mp 179°–180° C. (dec), $[\alpha]_D = 27.2°$ (C = 1.0, methanol).

In a process analogous to Example 7 the following compound is prepared.

EXAMPLE 9

(S)-α-Amino-10,11-dihydro-5H-dibenzo[a,d]cycloheptene-5-acetic acid

Step A: Preparation of 10,11-Dihydro-5H-dibenzo[a,d]cycloheptene-5-acetic acid; mp 167°–168° C.

Step B: Preparation of (4S-cis)-3-[(10,11-Dihydro-5H-dibenzo[a,d]cycloheptene-5-yl)acetyl]-4-methyl-5-phenyl-2-oxazolidinone; mp 130°–131° C.; $[\alpha]_D = -14.0°$ (C = 1.0, CHCl₃).

Step C: Preparation of [4S-[3(S*),4α, 5α]-3-[Azido(10,11-dihydro-5H-dibenzo[a,d]cycloheptene-5-yl) acetyl]-4-methyl-5-phenyl-2-oxazolidinone; mp 169°–171° C.; $[\alpha]_D = +179.4°$ (c = 1.0, CHCl₃).

Step D: Preparation of (S)-α-Azido-10,11-dihydro-5H-dibenzo [a,d]cycloheptene-5-acetic acid; mp 99°–101 ° C.; $[\alpha]_D = +37.8°$ (C = 1.0, CH₃OH).

Step E: Preparation of (S)-α-Azido-10,11-dihydro-5H-dibenzo [a,d]cycloheptene-5-acetic acid, hydrochloride; mp 316°–318° C. (dec.); $[\alpha]_D = +45.6°$ (C = 1.0, CH₃OH).

Step F: Preparation of (S)-α-Amino-10,11-dihydro-5H-dibenzo [a,d]cycloheptene-5-acetic acid Using the methodology of Example 1 (Step D) the title compound is prepared from (S)-α-amino-10,11-dihydro-5H-dibenzo[a,d]cycloheptene-5-acetic acid, hydrochloride.

In a process analogous to Example 8, the following compound is prepared.

EXAMPLE 10

N-Tertiary-butyloxycarbonyl-L-α-amino-10,11-dihydro-5H-dibenzo[a,d]cycloheptene-5-acetic acid; mp 178°–179° C.; $[\alpha]_D = -31.4°$ (c = 1.0, methanol).

EXAMPLE 11

N-Tertiary-butyloxycarbonyl-DL-α-amino-10,11-dihydro-5H-dibenzo[a,d]cycloheptene-5-acetic acid;

DL-Bhg.HCl (1.70 g, 5.43 mmol) is suspended in 150 mL of p-dioxane:H₂O (2:1) at room temperature. To the stirred solution is added 1.40 g (6.42 mmol) of di-tert-butyldicarbonate. The pH of the solution is adjusted to >9.0 with 1N NaOH and maintained at between pH 9 and 10 with alicelot additions of 1N NaOH, until the pH is constant. The solution is concentrated under reduced pressure to approximately 75 mL, overlain with ethyl acetate (50 mL) and acidified to approximately pH 2.5 with 10% aqueous HCl. The organic layer is separated, washed successively with 10% aqueous HCl (2×50 mL), brine (2×50 mL), H₂O (3×50 mL), and dried with MgSO₄. The solution is filtered, concentrated under reduced pressure, and the oil is recrystallized from ethyl acetate:heptane (1.82 g). The white solid is characterized by proton NMR, fast atom bombardment mass spectrometry (M+1 = 368) and elemental analysis.

EXAMPLE 12

(R)-α-Amino-5H-dibenzo[a,d]cycloheptene-5-acetic acid

Step A: Preparation of 5H-Dibenzo[a,d]cycloheptene-5-acetic acid

A round-bottom flask, equipped with a distillation apparatus, is charged with dibenzosuberenol (10.0 g, 48.01 mmol) and malonic acid (25.0 g, 240.08 mmol). The mixture is heated in a 160° C. oil bath. The solids melt. Gas bubbles form and water and acetic acid are distilled through the condenser. After 1.5 hours, the mixture is cooled to room temperature and dissolved in ethyl acetate. The organic solution is washed with brine and dried over MgSO₄. The solvent is removed in vacuo to give an off-white solid, which is recrystallized from hexane-ethyl acetate- (AcOEt)/1:1 to yield the title compound as white crystals, 10.2 g; mp 167°–168° C.

Step B: Preparation of (4R-cis)-3-[(5H-Dibenzo[a,d]cycloheptene-5-yl)acetyl]-4-methyl-5-phenyl-2-oxazolidinone A solution of acid from Step A (6.0 g, 23.97 mmol) in anhydrous ethylene glycol dimethyl ether (DME) (30 mL) is cooled to −20° C., under nitrogen (N₂), and freshly distilled diisopropyl-ethylamine (5.0 mL, 28.77 mmol) is added, followed by slow addition of pivaloyl chloride (3.2 mL, 26.37 mmol). The resulting milky slurry is stirred at −20° C. for 30 minutes. The white solid is filtered, washed with DME (5 mL). The lilt rate of the mixed anhydride is cooled to −78° C. under nitrogen atmosphere. In a separate flask, (4R)-methyl-(5S)-phenyl-2-oxazolidinone (4.7 g, 26.37 mmol) is dissolved in freshly distilled tetrahydrofuran (THF) (53 mL) and cooled to −78° C., under argon (Ar). Several crystals of triphenylmethane (Ph₃CH) is added as an indictor. To this solution is added n-butyllithium (n-BuLi) (17.3 mL, 27.81 mmol, 1.6M solution in hexane). The red solution is stirred at −78° C. for 5 minutes, and the solution of mixed anhydride prepared as described above, is added via cannula. The resulting light yellow solution is stirred at −78° C. for 15 minutes and then warmed to room temperature over 2 hours. The reaction is quenched by addition of aqueous ammonium chloride ($NH_4Cl$). The THF is removed in vacuo and the residue is extracted with dichloromethane ($CH_2Cl_2$) (3×100 mL). The organic extracts are combined and washed successively with aqueous sodium bicarbonate solution brine ($NaHCO_3$), dried over $MgSO_4$, and concentrated in vacuc. The resulting yellow solid is recrystallized from hexane-AcOEt/2:1 to give the title compound as a white solid, 6.3 g; mp 172°–173° C., $[\alpha]_D = +10.1°$ (c=1.0, $CHCl_3$).

Step C: Preparation of [4R-[3(R*),4a,5S]]-3-[Azido-(5H-dibenzo[a,d]cycloheptene-5-yl)acetyl]-4-methyl-5-phenyl-2-oxazolidinone To a solution of acyloxazolidinone from Step B (5.0 g, 12.21 mmol) in freshly distilled THF (162 mL), at −78° C., under At, was added KHMDS (26.9 mL, 13.43 mmol, 0.5M solution in toluene) dropwise. The yellow solution is stirred at −78° C. for 30 minutes, and a solution of 2,4,6-triisopropyl-benzenesulfonylazide (Example B) (4.9 g, 15.87 mmol) in dry THF (10 mL) is added. After 2 minutes at −78° C., acetic acid (AcOH) (2.5 mL, 43.96 mmol) is added quickly and the mixture is heated on a steam bath immediately to 30° C., and then stirred at room temperature for 2 hours. The mixture turns milky. The THF is removed in vacuo, and the resulting off-white paste is dissolved in $CH_2Cl_2$ (400 mL), washed successively with half saturated brine and half saturated $NaHCO_3$ solution, dried over $MgSO_4$. Evaporation of solvent in vacuo gave an off-white solid, which is recrystallized from hexane-AcOEt 1.5:1, to give the title compound as white crystals, 4.7 g; mp 175° C., $[\alpha]_D = -119.4°$ C. (c=1.0, $CHCl_3$).

Step D: Preparation of (R)-α-Azido-5H-dibenzo[a,d]cycloheptene-5-acetic acid

To a solution of the azide from Step C (0.87 g, 1.93 mmol) in 4:1 THF-$H_2O$ (20 mL), at 0° C., is added a solution of lithium hydroxide ($LiOH.H_2O$) (0.16 g, 3.86 mmol) in hydrogen peroxide ($H_2O_2$) (1.10 mL, 9.65 mmol, 30% aqueous) dropwise, under nitrogen. The milky mixture is stirred at 0° C. for 1 hour. Aqueous sodium sulfite ($Na_2SO_3$) (10 mL) is added. The bulk of THF is evaporated in vacuo. The aqueous solution is cooled in an ice bath and acidified with 6N HCl to pH 1. The white solid is extracted with $CH_2Cl_2$ (5X) and dried over $MgSO_4$. Evaporation of solvent in vacuo affords a yellow oil, which is purified by flash chromatography (silica gel, hexane-AcOEt-AcOH/100:50:1) to yield the title compound as a white solid, 0.5 g; mp 119°–120° C., $[\alpha]_D = -40.6°$ (c=1.0, MeOH). The chiral auxiliary is recovered as a white solid, 0.31 g; mp 120°–122 ° C.

Step E: Preparation of (R)-α-Amino-5H-dibenzo[a,d]cycloheptene-5-acetic acid, hydrochloride To a suspension of stannous chloride ($SnCl_2$) (0.41 g, 1.80 mmol) in MeOH (5 mL) is added the azido acid from Step D (0.35 g, 1.20 mmol). The reaction is exothermic. The cloudy mixture is stirred at room temperature for 1 hour and acidified with 6N HCl to pH 1. The solvent is removed in vacuo. The remaining slurry is purified by Dowex 50×8-100 ion exchange resin to give an off-white solid as the amino acid, 0.25 g. Part of this (0.15 g) is recrystallized in 3N HCl, to give the title compound as an off-white solid, as the amino acid hydrochloride, 0.21 g; mp 229°–232° C. (dec.), $[\alpha]_D$ +24.7° (c=1.0, MeOH).

Step F: Preparation of (R)-α-Amino-5H-dibenzo[a,d]cycloheptene-5-acetic acid

Using the methodology of Example 1 (Step D), the title compound is prepared from (R)-α-amino-5H-dibenzo[a,d]cycloheptene-5-acetic acid, hydrochloride.

EXAMPLE 13

N-Tertiary-butyloxycarbonyl-(R)-α-amino-5H-dibenzo[a,d]cycloheptene-5-acetic acid To a slurry of the amino acid hydrochloride (Example 12, Step E) (0.10 g, 0.37 mmol) in MeOH (5 mL), is added i-$Pr_2NEt$ (0.07 ml, 0.37 mmol), followed by $(Boc)_2O$ (0.16 g, 0.74 mmol). The mixture is stirred at room temperature overnight (18 hours), and concentrated in vacuo. The resulting yellow solid is flash chromatographed (silica gel, hexane-AcOEt-AcOH/100:50:1) to give the title compound as a white solid, 0.12 g; mp 150°–151° C. (dec.) , $[\alpha]_D = 27.3°$ (c=1.0, MeOH).

EXAMPLE 14

Ac—D—Bhg—Leu—Asp—Ile—Ile—Trp

The linear hexapeptide is prepared by standard solid phase synthetic peptide methodology utilizing a Boc/benzyl strategy (Stewart, J. M. and Young, J. D., *Solid Phase Peptide Synthesis*, Pierce Chemical Co., Rockford, Ill., 1984). All protected amino acids and reagents were obtained from commercial sources with the exception of N—α—Boc—DL—Bhg (Example 11) and are not further purified. The protected peptide resin is prepared on an Applied Biosystems 430A Peptide Synthesizer, utilizing protocols supplied for a dicyclohexylcarbodiimide-mediated coupling scheme (Standard 1.0, Version 1.40). Starting with 0.710 g of N—α—Boc—Trp—PAM resin (0.7 0 meq/g, 0.4 97 meq of Boc—Trp (For) total) the protected peptide is prepared by the stepwise coupling of the following amino acids (in order of addition): N—α—Boc—Ile∈0.5$H_2O$, N—α—Boc—Ile.0.5$H_2O$, N—α—Boc—Asp (Bzl) , N—α—Boc—Leu.$H_2O$, and N—α—Boc—DL—Bhg. A typical cycle for the coupling of an individual amino acid residue is illustrated below (reproduced from the ABI manual):

All the single couple RV cycles conform to the following pattern:
1) 33% TFA in DCM for 80 seconds
2) 50% TFA in DCM for 18.5 minutes
3) Three DCM washes
4) 10% DIEA in DMF for 1 minute
5) 10% DIEA in DMF for 1 minute
6) Five DMF washes
7) Coupling period
8) Five DCM washes After the coupling of N—α—Boc—DL—Bhg, the Boc group is removed with the end-$NH_2$ cycle (1.012 g).

The peptide is liberated from the solid support, and the carboxylate of aspattic acid deprotected by treatment with anhydrous hydrogen fluoride (9.0 mL) , anisole (0.5 mL), and dimethyl sulfide (0.5 mL) (60 minutes, 0° C.). After removing the hydrogen fluoride under a stream of nitrogen, the resin is washed with diethyl ether (3×30 mL) and extracted with 20% HOAc in water (3×30 mL) and glacial HOAc (2×30 mL). The aqueous extractions are combined, concentrated under reduced pressure, and lyophilized (360 mg). The crude peptide is dissolved in 4.0 mL of 50%

TFA/H2O, filtered through a 0.4 L syringe filter, and chromatographed on a Vydac 218TP 1022 column (2.2×25.0 cm, 15.0 mL/min, A: 0.1% TFA/H2O, B: 0.1% TFA/CH3CN, Gradient; 0% B for 10 minutes, 10% to 40% B over 120 minutes ). Two individual fractions are collected and combined based upon analysis by analytical HPLC. The combined fractions are concentrated separately under reduced pressure (10 mL), diluted with H2O (50 mL), and lyophilized (40.0 mg/ea). Separation into, the two diastereomers (Isomers A and B) is effected under these conditions ($t_R$=Isomer A 15.63 min, Isomer B 16.79 min). The late running peak fractions (Isomer B) are repurified under the same experimental conditions with a gradient of 30% to 50% B over 120 minutes at 15 mL/min to afford purified product. Acetylation is carried out with 20 mg of Isomer B in 90% acetic acid followed by addition of acetic anhydride (5 mL) and stirring overnight. After evaporation and drying the product Ac—D—Bh-g—Leu—Asp—Ile—Ile—Trp is 99% pure by HPLC. [Vydac 218 TP 1022 colunm (2.2×25.0 cm, 15.0 mL/min. A: 0.1% TFA/CH3CN, Gradient 20% to 86% B over 22 min.)] $t_R$=18.66 minutes. The homogeneity and structure of the resulting peptide is confirmed by analytical HFLC. Proton Nuclear Magnetic Resonance Spectroscopy ($H^1$-NMR) and Fast Atom Bombardment Mass Spectroscopy (FAB-MS), M+1 972.0, M Na+ 995.9.

PREPARATION OF STARTING MATERIALS

Example A (4R,5S)-4-Methyl-5-phenyl-2-oxazolidinone

A round bottom flask, equipped with a distillation apparatus, is charged with (1S,2R)-norephedrine (18.16 g, 99.1 mmol), diethyl carbonate (27.6 mL, 228 mmol), and potassium carbonate (28.9 g, 209 mmol), and heated at 160° C. (oil bath temperature). The distillation head temperature remained at ca 80° C. when ethanol is collected in the collection flask, which is cooled in an ice bath. When the head temperature drops to 60° C. (ca 5 hours), the oil bath is removed and the mixture is cooled to room temperature. The mixture is diluted in dichloromethane and washed with water (2X) and dried (magnesium sulfate). Concentration in vacuo affords an off-white solid (17.88 g), which is recrystallized in hexane-ethyl acetate 1:1.5, to afford the title compound as white crystals, 15.2 g; mp 120°-121° C., [α]$_D$=171.4° (2.042% in chloroform).

Example B 2,4,6-Triisopropylbenzenesulfonyl azide

To a stirred solution of 2,4,6-triisopropylbenzenesulfonyl chloride (18.2 g, 60.0 mmol) in reagent acetone (70 mL) is added a solution of sodium azide (4.3 g, 60 μmol) in ethanol-H2O 1:1 (40 mL). The temperature of the mixture rises from 21° C. to 29° C. during the addition. After stirring at room temperature for 2 hours, the reaction mixture is partitioned between dichloromethane and half saturated brine. The aqueous solution is extracted with dichloromethane (3X), the combined organic solution is washed with half saturated brine, and dried (magnesium sulfate). Removal of solvent in vacuo gives a colorless oil which is purified by flash chromatography (silica gel, hexane-ethyl acetate/4:1) to yield the title compound as a white solid, 18.5 g; mp 44°-44.5° C. (Evans, D., et al, *Journal of the American Chemical Society* 112:4011 (1990); mp 43°-44° C.).

We claim:

1. A compound of Formula I

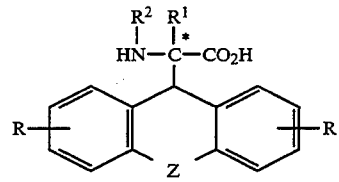

wherein Z is

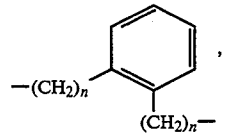

wherein n is zero or an integer of 1 or 2,

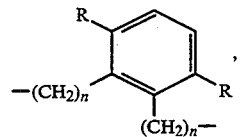

wherein R is as defined hereinafter and n is as defined above,

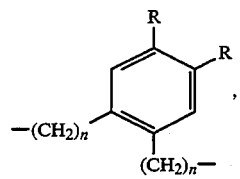

wherein R is as defined hereinafter and n is as defined above,

R is
  hydrogen,
  methyl,
  trifluoromethyl,
  methoxy,
  hydroxy,
  chloro,
  bromo,
  fluoro,
  iodo,
  2,4-dibromo,
  2,4-dichloro, and
  2,4-difluoro;
$R^1$ is
  hydrogen,
  alkyl,
  alkenyl,
  alkynyl,
  cycloalkyl,
  cycloalkylalkyl,
  aryl,
  arylalkyl,
  heteroaryl, and
  fluorenylmethyl;
$R^2$ is
  hydrogen, benzyloxycarbonyl,
tertiary-butyloxycarbonyl,
fluorenyloxycarbonyl,
1-adamantyloxycarbonyl,
2-adamantyloxycarbonyl, and
wherein R³ is hydrogen,
alkyl,
alkenyl,
alkynyl,
cycloalkyl,
cycloalkylalkyl,
aryl,
heteroaryl,
fluorenylmethyl,
$CX_3$, wherein X is halogen or aryl;
stereochemistry at C is D, L, or DL; or a pharmaceutically acceptable salt thereof.
* * * * *

UNITED STATES PATENT AND TRADEMARK OFFICE
CERTIFICATE OF CORRECTION

PATENT NO. : 5,380,925
DATED : January 10, 1995
INVENTOR(S) : Beylin et al

It is certified that error appears in the above-indentified patent and that said Letters Patent is hereby corrected as shown below:

Column 42, line 10, replace "C" with --$\overset{*}{C}$--.

Signed and Sealed this

Seventeenth Day of October, 1995

Attest:

BRUCE LEHMAN

*Attesting Officer*      *Commissioner of Patents and Trademarks*